Figure 1:
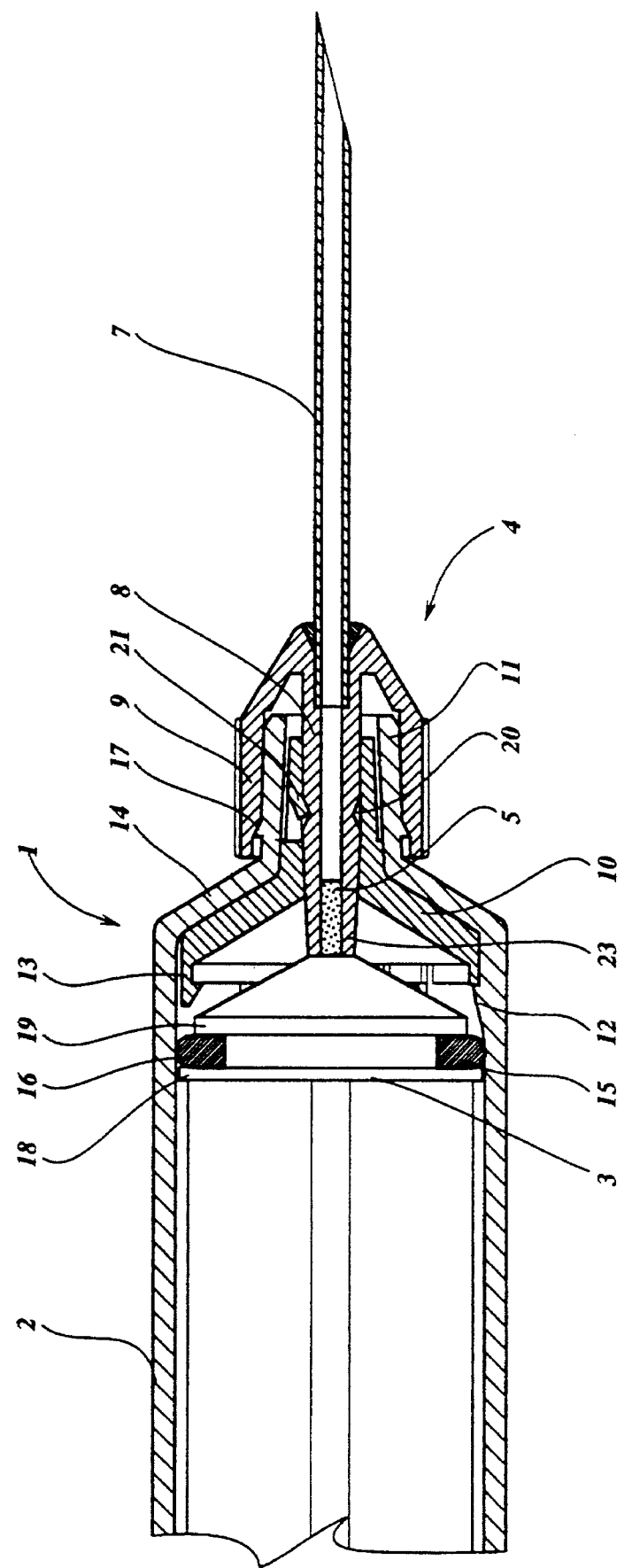

United States Patent [19]

van den Haak

[11] Patent Number: 5,466,226
[45] Date of Patent: Nov. 14, 1995

[54] INJECTION ASSEMBLY WITH A SUCTION NEEDLE AND A RETRACTABLE INJECTION NEEDLE

[75] Inventor: Abraham van den Haak, Eesergroen, Netherlands

[73] Assignee: A.P.I.S. Medical B.V., Eesergroen, Netherlands

[21] Appl. No.: 288,105

[22] Filed: Aug. 10, 1994

[30] Foreign Application Priority Data

Jul. 15, 1994 [NL] Netherlands ............. 9401174

[51] Int. Cl.⁶ .................................................. A61M 5/32
[52] U.S. Cl. ................................................ 604/192; 604/195
[58] Field of Search ......................... 604/110, 192, 604/195, 196, 240, 242, 243

[56] References Cited

U.S. PATENT DOCUMENTS

| | | | |
|---|---|---|---|
| 5,047,016 | 9/1991 | Dolgin et al. | 604/110 |
| 5,098,390 | 3/1992 | Wallingford | 604/195 |
| 5,188,597 | 2/1993 | Sweeney et al. | 604/110 |
| 5,263,934 | 11/1993 | Haak | 604/110 |
| 5,318,536 | 6/1994 | Williams | 604/110 |
| 5,328,475 | 7/1994 | Chen | 604/110 |
| 5,364,359 | 11/1994 | van den Haak | 604/110 |

FOREIGN PATENT DOCUMENTS

WO91/12842 9/1991 WIPO.
WO92/05817 4/1992 WIPO.

*Primary Examiner*—John D. Yasko
*Assistant Examiner*—Adam J. Cermak
*Attorney, Agent, or Firm*—Kenyon & Kenyon

[57] ABSTRACT

An injection assembly comprising a liquid container with an outflow opening and a piston displaceable therein, a suction needle with a needle fitting which is adapted to be releasably fitted in the outflow opening of the liquid container, and an injection needle with a needle fitting which is adapted to be permanently fixed on the outflow opening of the liquid container, said assembly further comprising an auxiliary coupling part which is fixed in the outflow opening of the liquid container, which is connected with the needle fitting of the injection needle and which comprises second coupling means which are permanently coupled with the first coupling means of the piston in the presence of the injection needle, which coupling cannot take place in the presence of the suction needle.

20 Claims, 13 Drawing Sheets

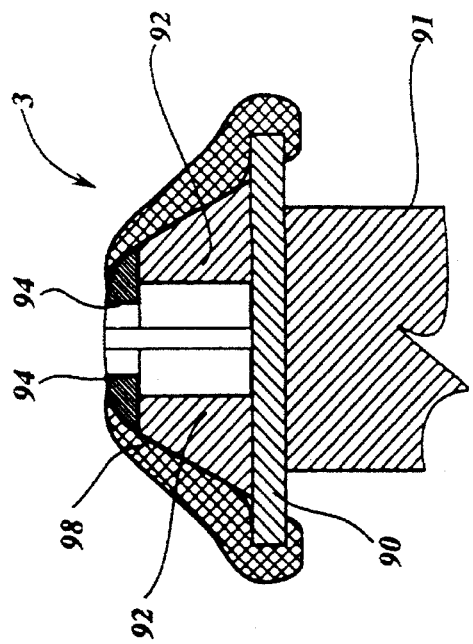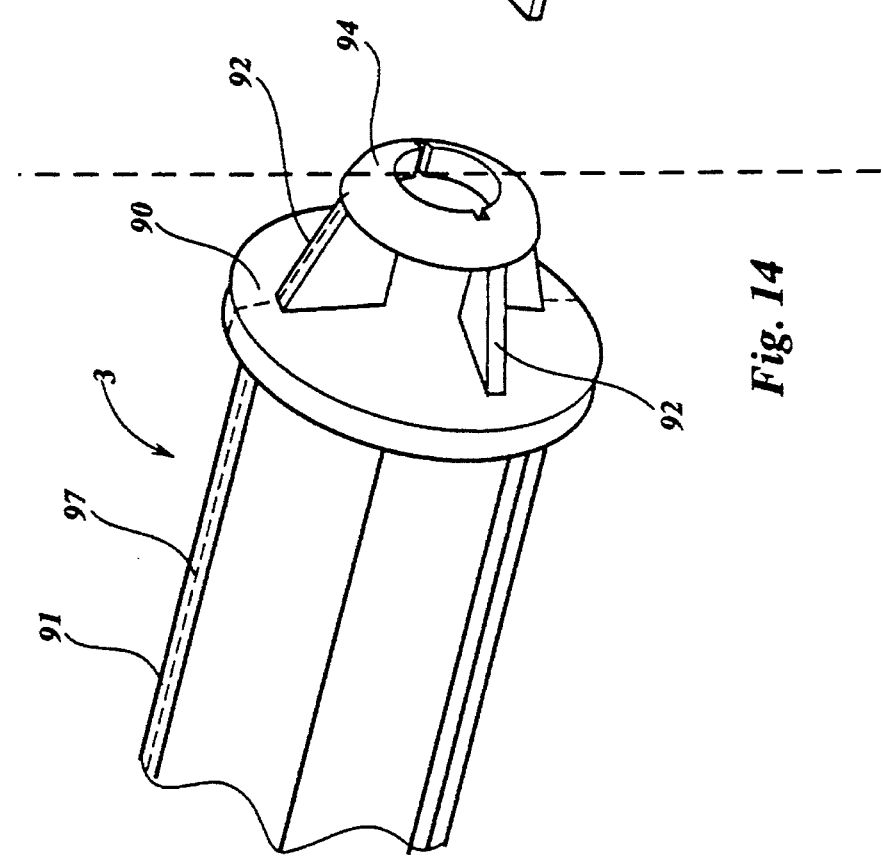

INJECTION ASSEMBLY WITH A SUCTION NEEDLE AND A RETRACTABLE INJECTION NEEDLE

The present invention relates to an injection assembly, comprising at least:

a liquid container with an outflow opening;

a piston displaceable in said liquid container;

a suction needle with a needle fitting which is adapted to be releasably fitted on or in the outflow opening of the liquid container; and an injection needle with a needle fitting which is adapted to be permanently fixed on or in the outflow opening of the liquid container;

in which the piston comprises first coupling means which are adapted to be coupled directly or indirectly with the needle fitting of the injection needle, in order to allow the injection needle being retracted into the liquid container after use, safety means being present for preventing that the first coupling means of the piston will form a coupling during displacement of the piston in the presence of the suction needle.

Such an injection assembly is known from WO-A 91/12842. Said international patent application discloses an injection assembly with a retractable injection needle. The injection needle comprises a needle fitting which is fixed in the outflow opening of the liquid container, and which, during the second stroke of the piston, i.e. after sucking in liquid, can be coupled with the piston in order to allow the needle to be retracted into the container. In this patent application reference is made to the fact that, for sucking in liquid, also a suction needle can be applied. The manner in which this is to be done is, however, not described in detail.

The use of a suction needle has a number of important advantages. A needle with a relatively large diameter can be chosen, so that the liquid container can be quickly filled. Often the needle is inserted through a septum into a medicine vial, so that the needle tip can damaged and the outer side of the needle can be contaminated, which, as a matter of course, is undesirable for an injection needle. In the case of glass vials which are opened by breaking off a glass cap, there is a danger that the needle is damaged when inserting it into the opening. Moreover an injection needle can have a form which is unsuitable for sucking in liquid from a medicine vial, for instance because it is too short. The use of a separate suction needle ensures that always an undamaged and sterile injection needle can be used for injection into a patient.

After use of the assembly, the injection needle can be retracted into the liquid container, and re-using the needle can be prevented by suitable means.

According to WO-A 91/12842, during the liquid suction stroke of the piston a coupling between the piston and the needle fitting of the injection needle is prevented in that the piston consists of two relatively movable parts, i.e. a piston rod with a head which is displaceable in respect of this rod. A draw-back thereof is that the piston can be moved to and fro only once without coupling, since, in fact, the second time a coupling with the needle fitting of the injection needle takes place.

It is an object of the present invention to provide an injection assembly not having these draw-backs, which, with other words, can be displaced to and fro as many times as required during sucking in liquid without a coupling between the piston and the other parts taking place. An other object of the invention is to provide an injection assembly with a simpler structure and being more easily to handle.

To that end the invention is characterised in that the assembly comprises, moreover, an auxiliary coupling part which is or can be fixed in the outflow opening of the liquid container, which, on the one hand, is or can be connected with the needle fitting of the injection needle, and which, on the other hand, comprises second coupling means which can be permanently coupled with the first coupling means of the piston in the presence of the injection needle, which coupling, however, cannot take place in the presence of the suction needle.

In the injection assembly according to the invention, no movable parts are present anymore on the piston, which, therefore, has a simpler construction, which injection assembly can, moreover, very easily be manipulated.

Preferably, in a first embodiment of the injection assembly according to the invention, the auxiliary coupling part is formed as a substantially funnel-shaped part which substantially fits in the extremity of the liquid container near the outflow opening, said auxiliary coupling part comprising third coupling means which can be permanently coupled with the portion of the needle fitting of the injection needle to be inserted into the outflow opening, the second coupling means of the auxiliary coupling part being in the form of one or more claws, the first coupling means on the piston then having the form of an annular collar with which the claws can form a permanent coupling, the liquid container comprising, near the second coupling means of the auxiliary coupling part, one or more lugs for positioning the auxiliary coupling part, which lugs can be released by the piston, and the suction needle fitting comprising a portion to be inserted into the outflow opening and having such a length that the claws of the auxiliary coupling part in the presence of the suction needle cannot be coupled with the annular collar on the piston.

The auxiliary coupling part constructed in this manner is present in the container in a very stable manner, whereas, in the presence of the suction needle, a coupling between the piston and the claws on the auxiliary coupling part cannot take place, independently of the number of strokes of the piston. In practice, the injection assembly according to this embodiment can be supplied with a suction needle fitted thereon.

In this embodiment the third coupling means are preferably formed as one or more lips curved towards the longitudinal axis of the assembly, and the portion of the suction needle fitting to be inserted into the outflow opening advantageously comprises an annular groove for accommodating said lips, and, furthermore, the portion of the injection needle fitting to be inserted into the outflow opening comprises a collar for a permanent coupling with the lips. Since the respective parts are generally made of plastics, the inwardly directed lips will, when being moved outwardly in the presence of a suction needle fitting, lose their elasticity in the course of time. Therefore it is preferred to provide, in the suction needle fitting, an annular groove for accommodating said lips.

In a second preferred embodiment of the injection assembly according to the invention, the auxiliary coupling part is substantially tubular, and the second coupling means are in the form of one or more movable lips with claws, the third coupling means comprising an annular groove which, on the one hand, can releasably cooperate with the needle fitting of the suction needle, and, on the other hand, can permanently be coupled with the needle fitting of the injection needle, the claws of the second coupling means being adapted to cooperate with a recess in the extremity of the piston, and, furthermore the outflow opening is provided at the inner side with fourth coupling means with two positions which are adapted to cooperate with fifth coupling means at the outer side of the auxiliary coupling part, all this in such a manner, that, on the one hand, in the presence of the suction needle, the claws of the second coupling means cannot cooperate with the recess in the piston and the fifth coupling means can cooperate with the fourth coupling means in the first position, and, on the other hand, in the presence of the injection needle, the claws of the second coupling means can cooperate with the recess in the piston, since, when putting on the injection needle, the coupling between the fourth and the fifth coupling means is brought into the second position.

In this embodiment, the auxiliary coupling part is, in the presence of the suction needle, in a non-operative condition, i.e. the first coupling position, on which moment the piston can be moved to and fro as often as required without a coupling taking place in this case. On the moment that the injection needle is fixed, the auxiliary coupling part is brought into the second operative position, at which moment the coupling between the second coupling means on the auxiliary coupling part and the first coupling means on the piston can take place.

In a particular case of this embodiment, the fifth coupling means of the auxiliary coupling part are preferably in the form of lugs on the lips of the claws of the second coupling means, and the fourth coupling means are formed on the inner wall of the outflow opening in the form of two circumferential recesses, the recess at the downflow side seen in the outflow direction of the outflow opening being chamfered towards the other recess, all this in such a manner, that, on the one hand, after inserting the auxiliary coupling part into the outflow opening and in the presence of the suction needle, the lugs on the lips of the claws can cooperate with the downflow recess, at which moment the claws of the second coupling means cannot be coupled with the piston, and, on the other hand, when putting on the injection needle, the lugs on the auxiliary coupling part can be moved into the other recess, at which moment a coupling of the claws with the piston is possible, during which coupling the coupling between the lugs and the recess can be released by bending the lips towards each other.

Advantageously the auxiliary coupling part forms, in this case, a part of the needle fitting of the injection needle. Therefore, in this embodiment, the auxiliary coupling part is, in the presence of the suction needle, not present in the outflow opening of the liquid container, so that an undesired coupling between the piston and the auxiliary coupling part can never occur.

Particularly advantageously the fourth coupling means are, in this case, made in the form of a circumferential recess or collar at the inner side of the outflow opening, and the fifth coupling means can cooperate therewith for coupling the auxiliary coupling part with the liquid container, which coupling can be released by coupling the piston with the auxiliary coupling part and by bending the lips towards each other.

The fixation of the needles in question on the needle fittings on or in the outflow opening of the liquid container can be done in many ways. Generally this takes place in that the outflow opening is provided with external screw thread, the needle fittings being provided with internal screw thread.

According to the invention the outflow opening of the liquid container is, in particular, made in the form of a tube section having a chamfered collar, and the needle fittings of the suction as well as the injection needle comprise a cap having an inner diameter which is smaller than the outer diameter of the chamfered collar. In this manner a good and dependable fixation by a kind of tight fit can be obtained, which, however, can be released in a simple manner by a slight rotation.

Advantageously the cap of the injection needle comprises one or more claws which can be permanently coupled with the chamfered collar on the outflow opening. This to prevent reuse after retraction of the injection needle into the liquid container. The cap with the needle fitting cannot be removed from the outflow opening.

Current injection and suction needles comprise protection means for preventing the user to injure himself with the needles, e.g. in the form of a sleeve or the like. According to the invention, the suction needle as well as the injection needle comprise, preferably, a sheath which can be removed before use. In particular both sheaths are united as two sheath portions of one sheath, which provides a very easy handling. Both needles are, then, always together, and, when removing the suction needle from the liquid container, it can be re-inserted into the corresponding portion of the sheath, after which the injection needle can be arranged from the same sheath. In this manner the needles cannot get lost or unintentionally confused with other needles.

In a preferred embodiment the sheath portions are united with one another in such a manner that the needles can be inserted therein side by side but in the opposite direction, and at least one sheath portion comprises a closing cap which also fits on the other sheath portion.

In practice an injection assembly according to the invention will be supplied with the suction needle already mounted on the liquid container, and, in the other sheath portion, the injection needle is provided in the opposite direction. After use of the liquid container with the suction needle, the suction needle can be inserted into the corresponding sheath portion and can be removed from the liquid container. The cap can be removed from the sheath portion of the injection needle, and can be placed on the sheath portion of the suction needle, after which the injection needle can be fixed on the outflow opening by means of the compound sheath. Such a construction of the sheath portions prevents unnecessary injuries by needles with all the undesired consequences thereof, and provides a very easy handling.

Moreover the invention provides an auxiliary coupling part, intended for being used in an injection assembly according to the invention.

Furthermore the invention provides an injection needle and a suction needle, each comprising at least one needle and one needle fitting, intended for an injection assembly according to the invention.

Moreover a sheath is provided for an injection assembly according to the invention, at least comprising two oppositely directed sheath portions, intended for accommodating a suction needle and an injection needle.

Finally the invention provides a piston with a recess provided with an inwardly directed collar in the extremity thereof for use in an injection assembly according to the invention, comprising a piston rod with a front surface directed substantially transversely thereto, on which front surface an annular collar portion is supported by two or more supports, around which assembly a suitably shaped elastically deformable piston head can be arranged. The advantage of such a piston is that it can be manufactured in a very simple way with only one separate filler core and a two-part die, e.g. by injection moulding. This will be elucidated in more detail by reference to the drawings.

It is preferred, in the injection assembly according to the invention, to arrange locally in the bore of the suction needle a sieve or filter material, in order to prevent that undesired solid material can be sucked into the liquid container. This is, in particular, important in the case of medicine vials made of glass having a glass cap which is to be broken off, in which case often small glass splinters may fall into the vial.

The suction needle and the corresponding needle fitting can be made as a unitary structure, e.g. from plastics or metal.

Figure 2:
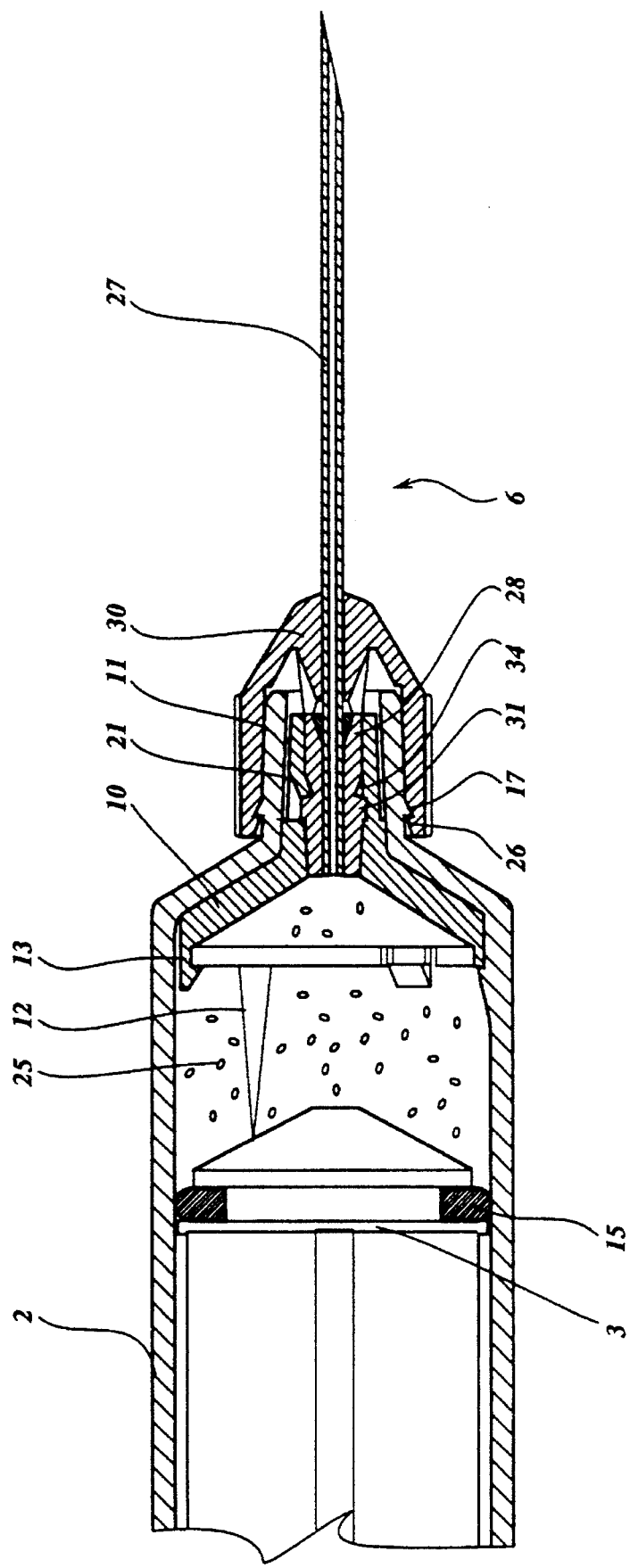
Figure 3:
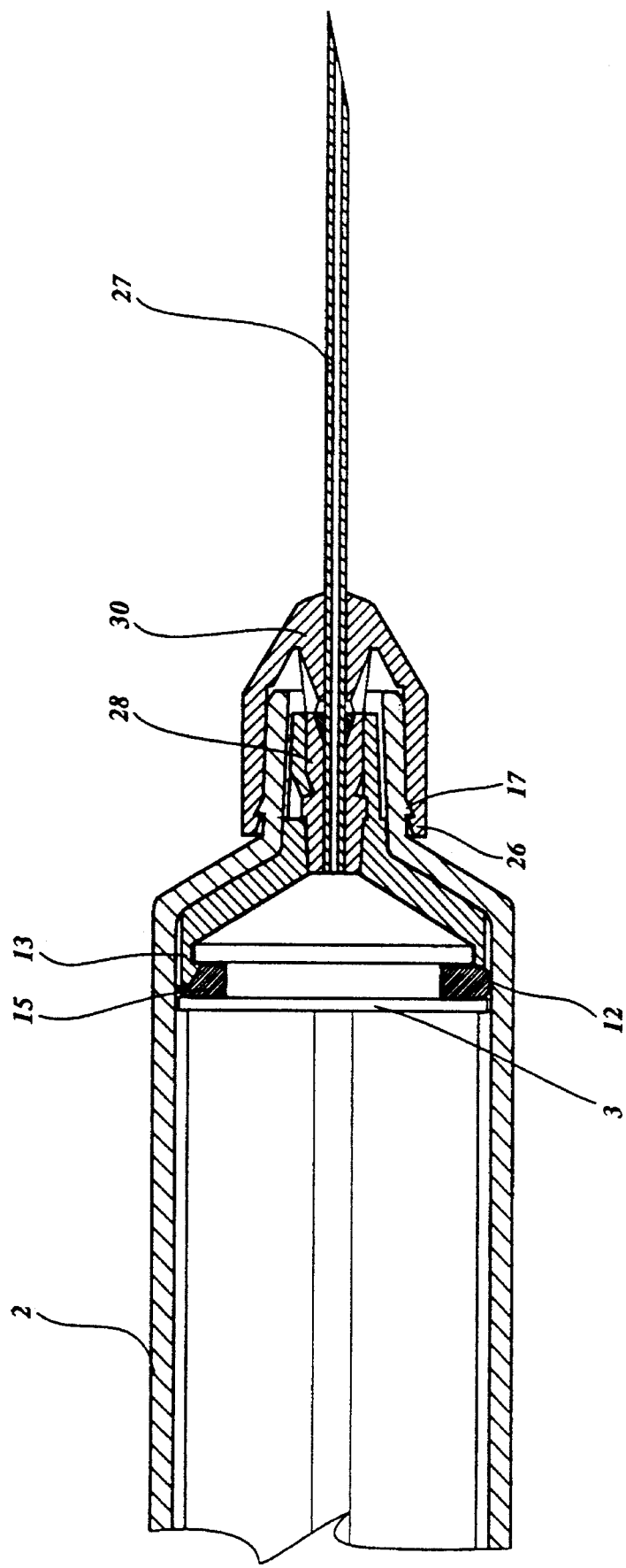
Figure 4:
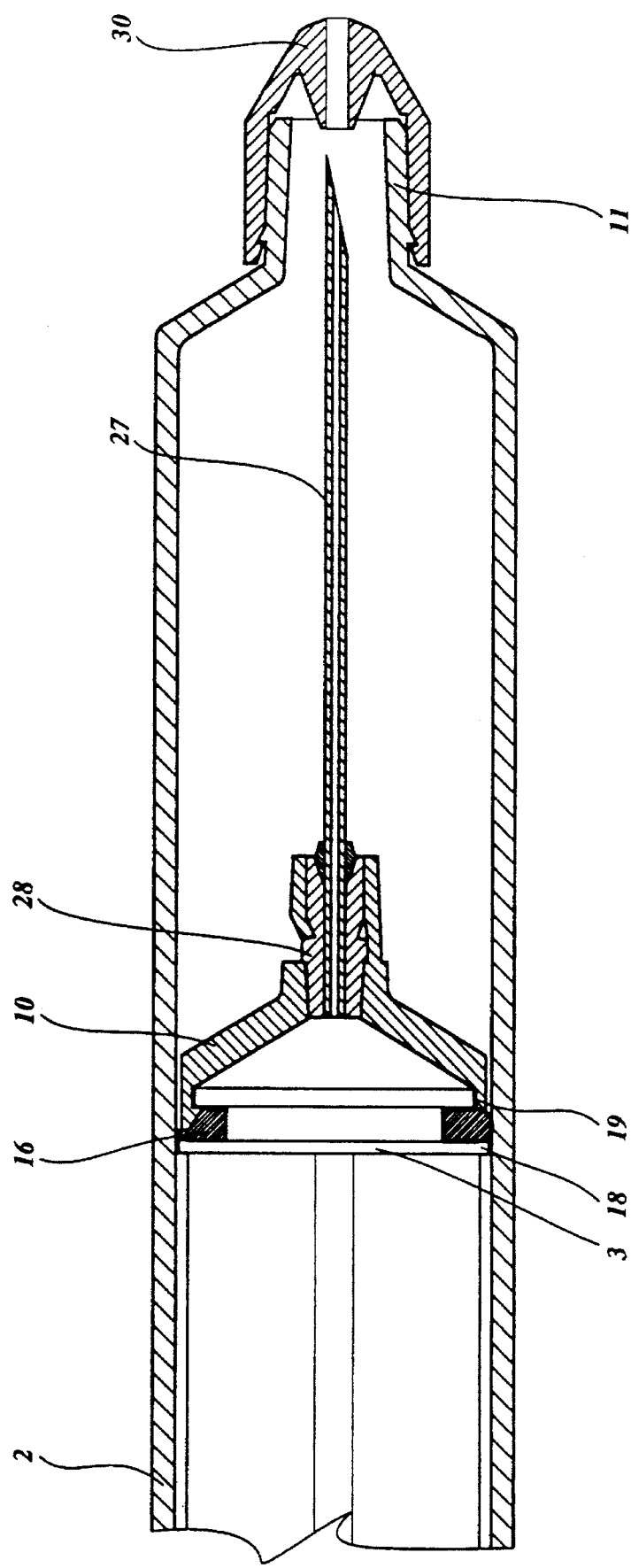
Figure 5:
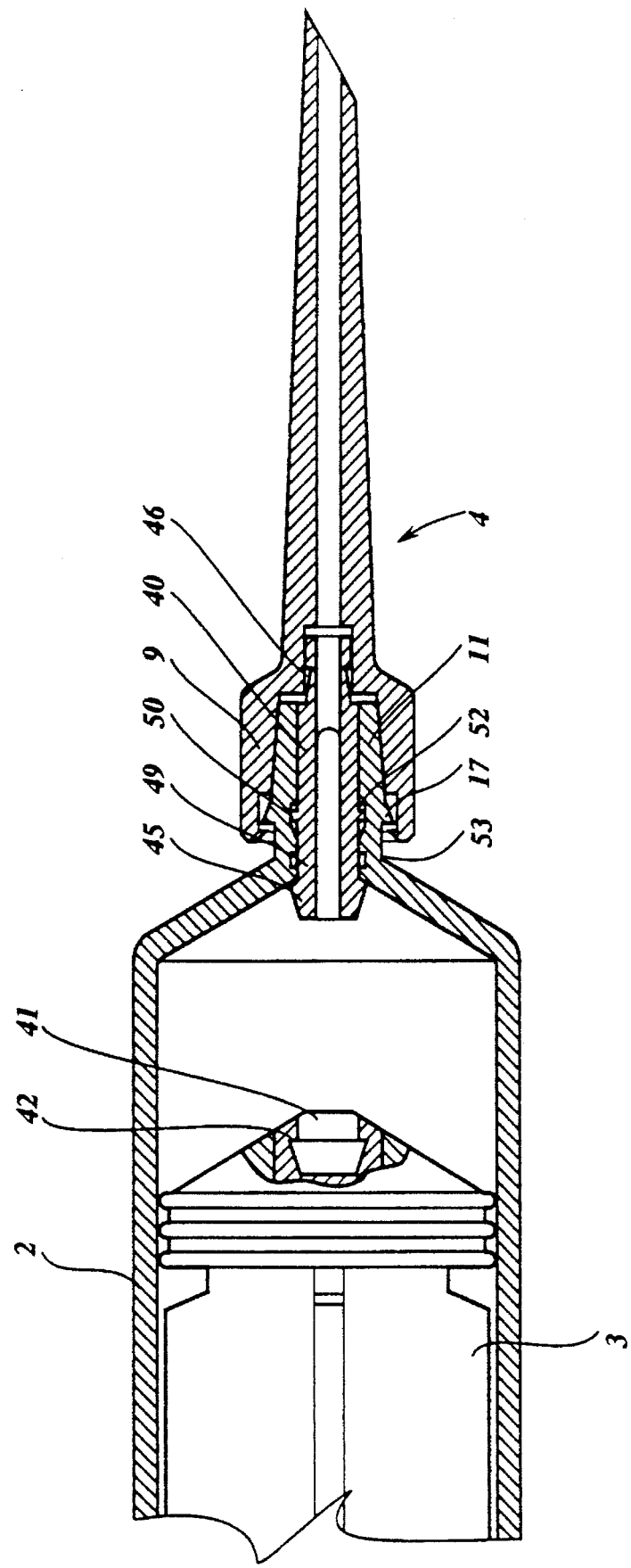
Figure 6:
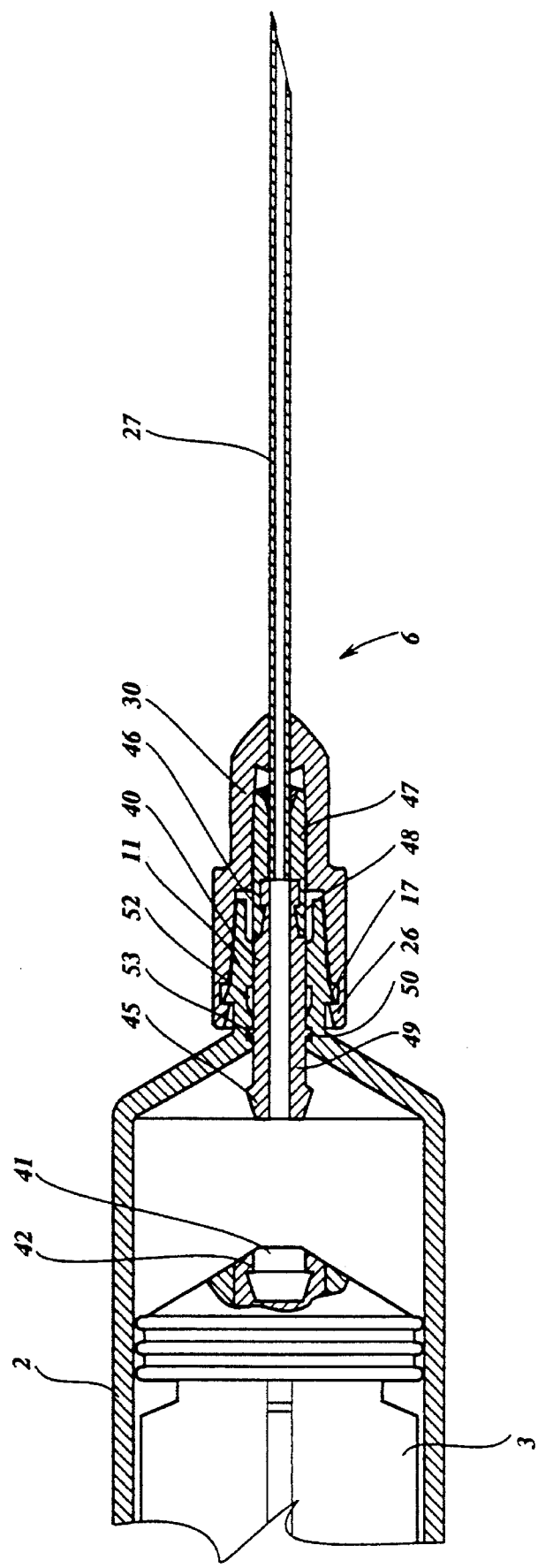
Figure 7:
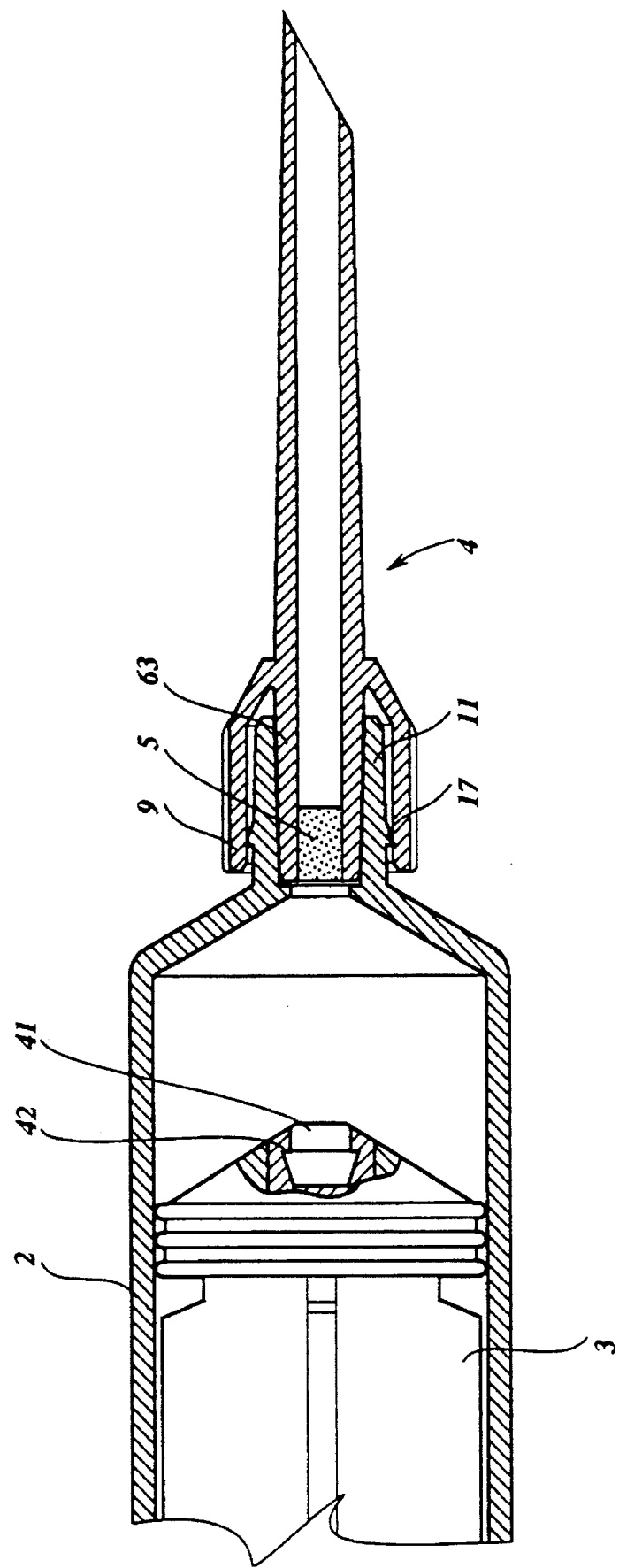
Figure 8:
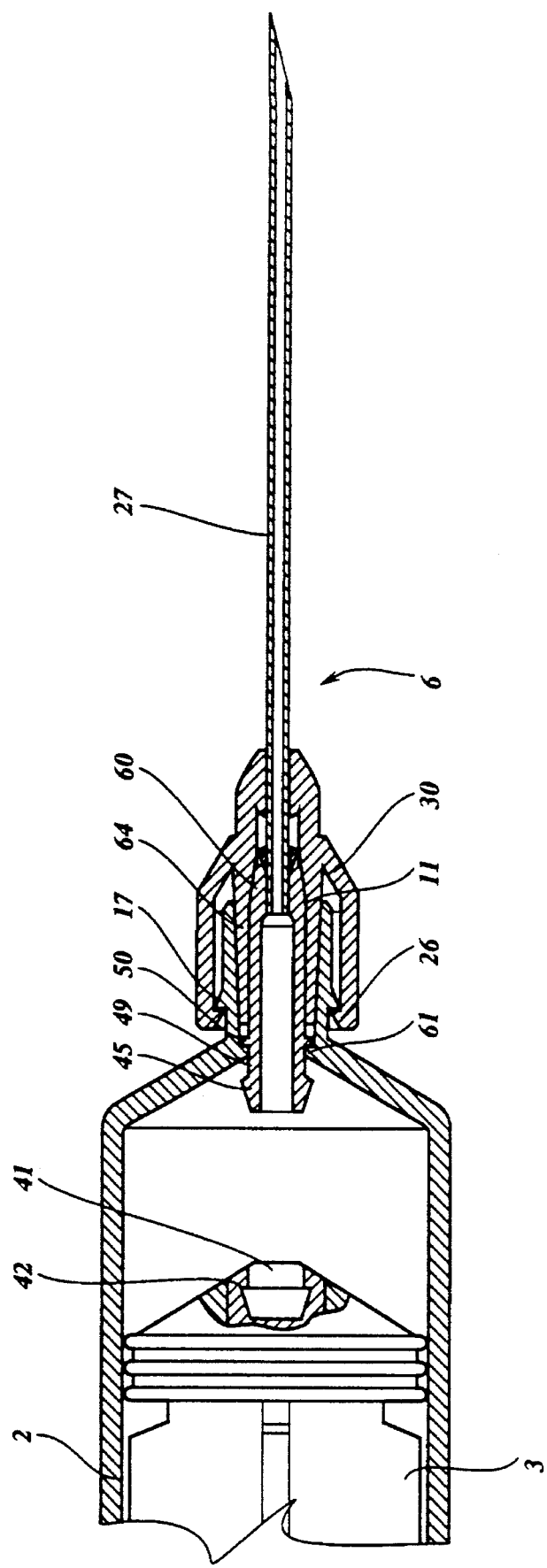
Figure 9:
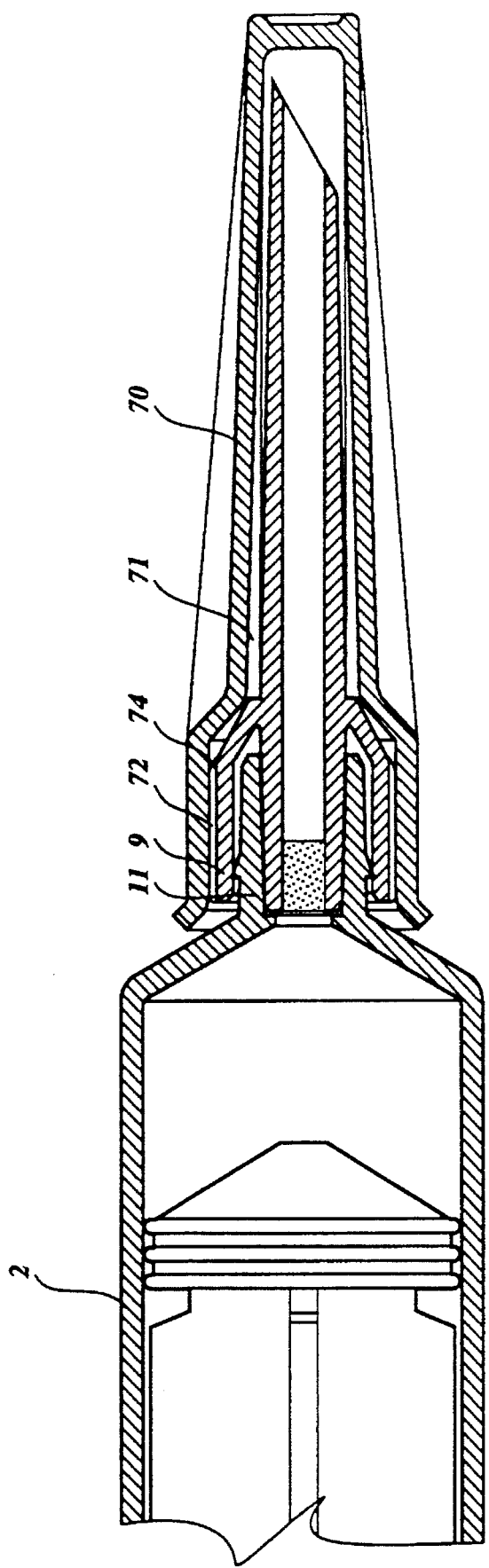
Figure 10:
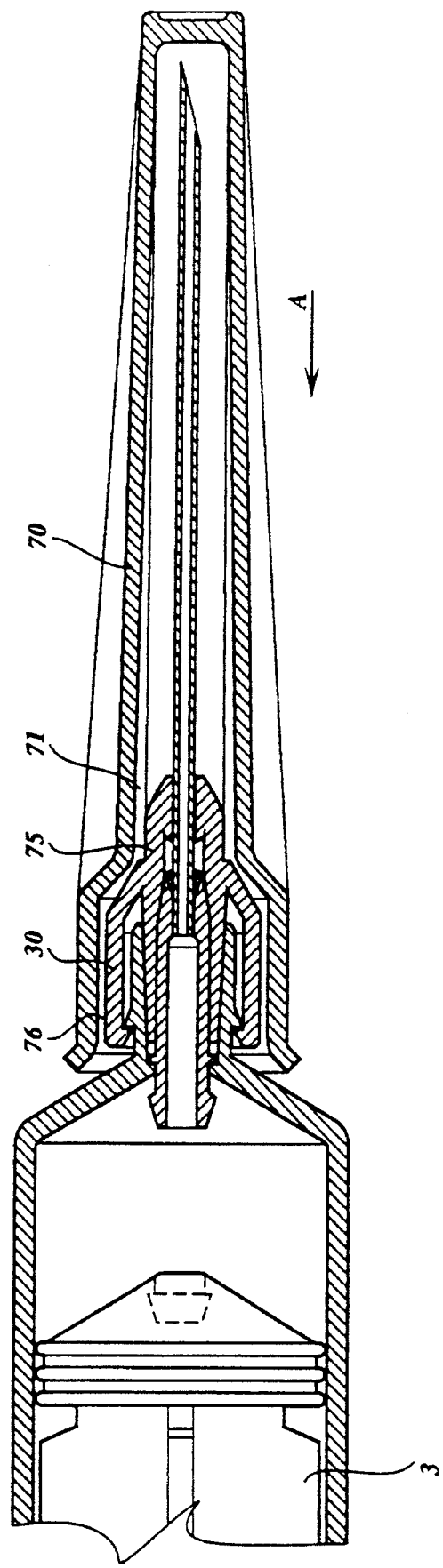
Figure 11:
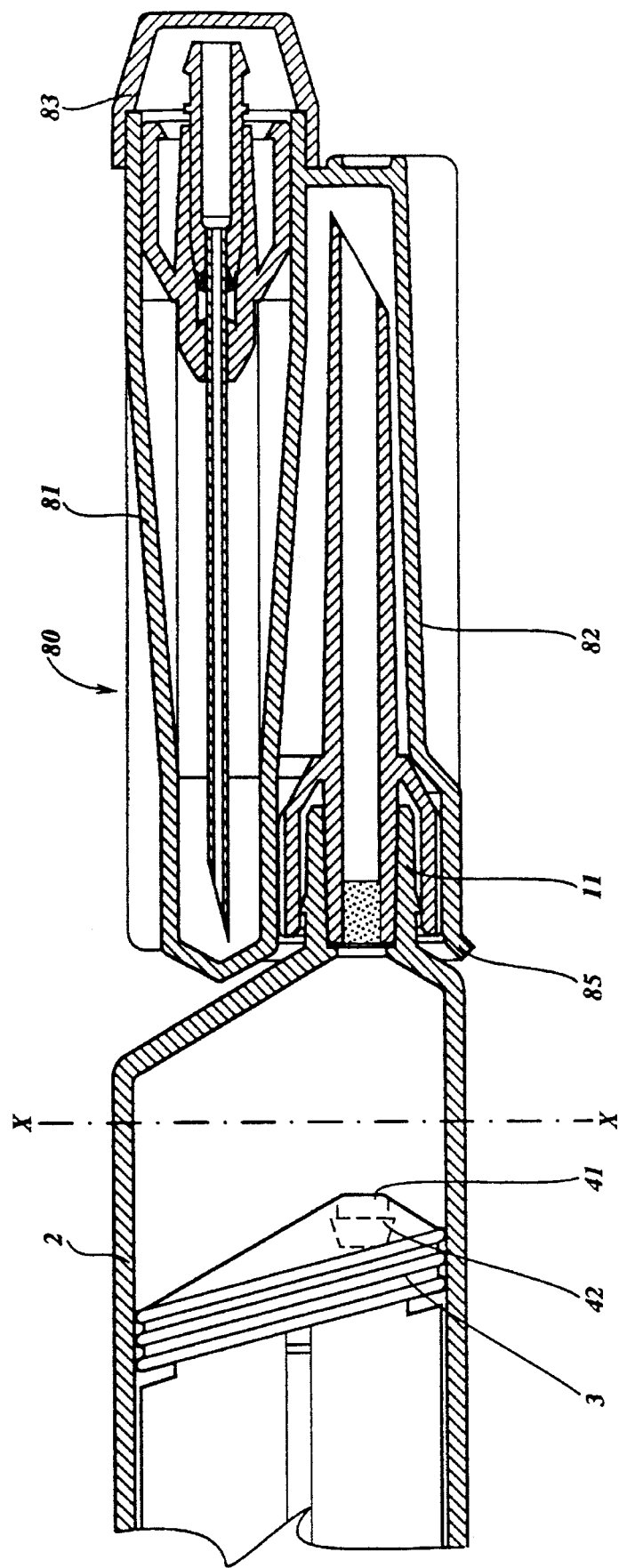
Figure 12:
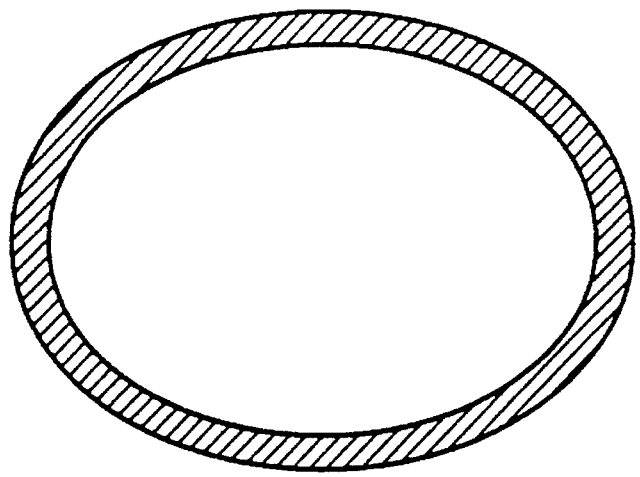
Figure 13:
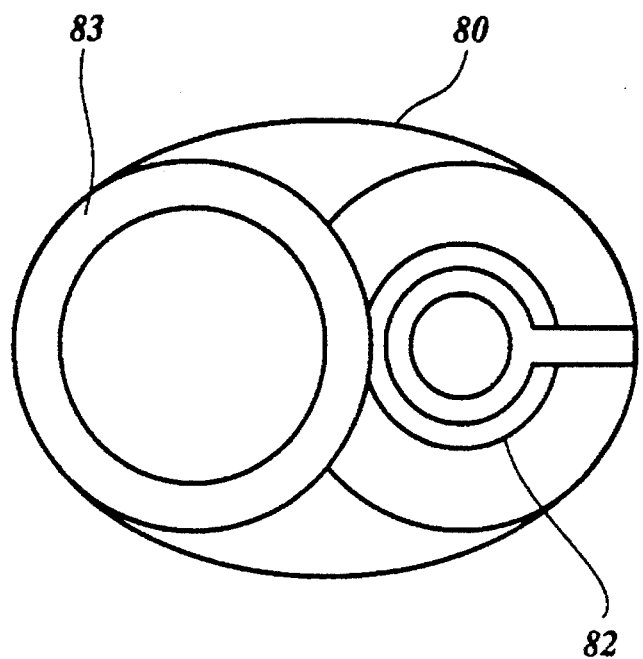

The invention will be elucidated below by reference to the appended drawing, showing in:

FIG. 1 an embodiment of an injection assembly according to the invention with a suction needle;

FIG. 2 the injection assembly of FIG. 1 with an injection needle;

FIG. 3 the injection assembly of FIG. 2 in which the auxiliary coupling part is coupled;

FIG. 4 the injection assembly of FIG. 2 in which the needle is retracted into the liquid container;

FIG. 5 another embodiment of an injection assembly according to the invention with a suction needle;

FIG. 6 the injection assembly of FIG. 5 with an injection needle;

FIG. 7 a simplified embodiment of the injection assembly of FIG. 5 with a suction needle;

FIG. 8 the embodiment of the injection assembly of FIG. 7 with an injection needle;

FIG. 9 the injection assembly of FIG. 7 with a sheath;

FIG. 10 the embodiment of FIG. 8 with a sheath;

FIG. 11 a special embodiment of the injection assembly according to the invention with a sheath with two sheath parts;

FIG. 12 a cross-section of the piston of the injection assembly of FIG. 11;

FIG. 13 a front view of the injection assembly of FIG. 11;

FIG. 14 a perspective view of the piston with a filling core; and

FIG. 15 a cross-section of the piston head with a rubber piston cap.

In FIG. 1 a first embodiment of the injection assembly according to the invention is diagrammatically shown at 1 and partially in section, which assembly comprises, substantially, a liquid container 2 with a piston 3 displaceable therein, a suction needle 4 and an injection needle 6 (which is shown in FIG. 2).

The suction needle 4 comprises a needle 7 with a cap 9, which is constructed as a unit together with the needle fitting 8. At 5 a filter is schematically shown, which serves to prevent that, undesiredly, solid matter such as glass splinters (as mentioned before) will be sucked into the liquid container 2.

In the liquid container 2 an auxiliary coupling part 10 is arranged which rests on lugs 12 on the inner wall of the liquid container 2. The auxiliary coupling part 10 comprises, on the one hand, a plurality of claws 13 (second coupling means) divided over the circumference, which can be permanently coupled with an annular recess 15 (first coupling means) on the piston 3 in which a sealing ring 16 is arranged. This recess 15 is defined between two parts 18 and 19 of the piston 3, the part 18 having a larger diameter than the part 19.

The outflow opening 11 of the liquid container 2 comprises an external collar 17 which cooperates with a friction fit with the inner wall 18 of the cap 9. The needle fitting 8 comprises an annular recess 20 which can cooperate with a lip 21, the latter being bent somewhat towards the longitudinal axis of the assembly.

The auxiliary coupling part 10 is confined between the lugs 12 on the inner wall of the liquid container 2 and the inner wall 14 of the liquid container 2.

The needle fitting 8 of the suction needle 4 comprises a portion 23 extending into the liquid container 2, serving as a stroke limiting means for the piston 3, thus providing safety means preventing that the coupling means 15 on the piston 3 will be coupled with the claws 13 in the presence of the suction needle 4, and, thereby, would no longer be able to provide the desired coupling with the injection needle 6 to be mounted after sucking. Generally an injection assembly according to the present embodiment will be supplied with the sucking needle already mounted thereon, and the injection needle 6 is separately supplied therewith. As will be discussed below in more detail, the suction needle 4 as well as the injection needle 6 comprise, on delivery, a sheath.

In FIG. 2 the injection assembly according to FIG. 1 is shown, on which an injection needle 6 is mounted. After sucking in a quantity of liquid 25 by means of the suction needle 4, the suction needle 4 can be removed from the outflow opening 11 by a rotating and pulling movement, if necessary by means of the sheath to be placed over the needle 4. Subsequently the injection needle 6, still present in its sheath, can be shifted over de outflow opening 11, the claws 26 then snapping behind the collar 17, so that the injection needle 6 cannot be removed anymore.

The injection needle 6 comprises a needle 27 and a needle fitting 28, as well as a separate cap 30. The needle fitting 28 comprises an annular collar 31 and a recess 34. The collar 31 is clamped between the inwardly curved lip 21 of the auxiliary coupling part 10 and a shoulder 32, the lip 21 being situated in the recess 34. In this manner said needle fitting 28 with the needle 27 is coupled unambiguously and in a permanent manner with the auxiliary coupling part 10.

Since injection needles are generally made from tubular material which is often supplied on large reels, these needles have always a slight curvature, so that after pulling inwards the needles through an opening 33 in the cap 30, the needle cannot be pushed outwards again. The passage 33 can also have an inclination in respect of the longitudinal axis of the assembly which has the same effect.

It will be clear that, in the condition shown in FIG. 2, the portion 18 of the piston 3, after pressing the liquid 25 through the injection needle 27, is capable to press the lugs 12 outwards, so that the annular recess 15 at 19 can be coupled with the claws 13 under deformation of the sealing ring 16. This condition is shown in FIG. 3.

During said coupling the lugs 12 are released by deformation of the liquid container 2, and the auxiliary coupling part 10 can be moved therealong, taking along the needle fitting 28 and the injection needle 27. In this manner the injection needle 27 is pulled into the liquid container 2. This condition with a retracted injection needle 27 is shown in FIG. 4. Thereafter and if required by pushing inwards again the piston in the known manner into the liquid container the needle can be made unusable, since it cannot move outwards again through the opening 33 and will be bent.

Re-using is prevented since the cap 30 cannot be removed from the outflow opening anymore because of the cooperation between the lugs 26 and the collar 17.

In FIGS. 5 and 6 another embodiment of the injection assembly according to the invention is shown, in which a tubular auxiliary coupling part 40 is used. Moreover, in this case, the piston 3 does not comprise an annular recess, but a central recess 41 with an inwardly directed collar 42. The suction needle 4 is made as a unitary structure with the cap 9, and can, for example, consist of metal or plastics. The auxiliary coupling part 40 comprises claws 45 on lips 49, which can cooperate with the collar 42 in the recess 41 of the piston 3 on the one hand, and comprises, on the other hand, an angular recess 46 which can cooperate with claws 48 on the needle fitting 47 of the injection needle 6.

The auxiliary coupling part 40 comprises, moreover, lugs 50 between the claws 45 and the annular recess 46, which are fixed on the lips 49. These lugs 50 form the fifth coupling means on the auxiliary coupling part 40, which can cooperate with fourth coupling means having two positions on the inner wall of the outflow opening 11.

These fourth coupling means comprise two recesses 52 and 53, the recess 52 being chamfered towards the recess 53. In the initial condition, and, as the case may be, in the presence of the suction needle, the auxiliary coupling part 40 is situated in the position shown in FIG. 5, i.e. the lugs 50 are present in the recess 52. When mounting the injection needle 6, the claws 48 snap into the recess 46 in the auxiliary coupling part 40, and the lugs 50 are forced from the recess 52 into the recess 53, the claws 45 then becoming free in the liquid container 2, so that they can be coupled with the collar 52 in the opening 41 of the piston 3. Just as in the preceding embodiment, the needle fitting 47 of the injection needle 6 is made separate from the cap 30, which, also in this case, is provided with snap lugs 26 which can snap behind the collar 17 for a permanent fixation thereof.

The advantage of this embodiment in comparison with the preceding embodiment shown in FIGS. 1–4 is that, in the initial condition in which the piston 3 bears against the claws 45 of the auxiliary coupling part 40, substantially no air is present in the liquid container 2, which can, therefore, be filled completely by suction, and that, when expelling the liquid in the presence of the injection needle, the liquid container can be substantially completely emptied, which, in the case of the embodiment shown in FIGS. 1–4, is the case only to a smaller extent.

FIGS. 7 and 8 show an injection assembly which is a simplified embodiment of the injection assembly according to FIGS. 5 and 6. Herein the auxiliary coupling part is formed as a unitary structure with the needle fitting 60 of the injection needle 6. This auxiliary coupling part and needle fitting 60 comprise again claws 45 at the ends of lips 49, which comprise, moreover, lugs 50. The fourth coupling means have only one position, and are, in this case, formed as an inwardly directed collar 61 in the outflow opening 11.

The advantage of this embodiment is that, when the suction needle 4 is present, there are no portions of the auxiliary coupling part present at all which extend into the liquid container, since the auxiliary coupling part forms a unit with the needle fitting 60 of the injection needle 6, so that any risk of coupling is avoided thereby.

As clearly appears from these Figs., the inner wall of the outflow opening 11 is made slightly conical, and the portion 63 of the suction needle as well as the portion 64 of the injection needle have been provided, at their outer side, with a correspondingly adapted shape, all this in order to obtain a very simple mounting with an extremely good sealing. The portion 64 forms, near the injection needle 6, one unit with the cap 30.

When the liquid container 2 has been filled with liquid by means of the suction needle, the suction needle is removed and the injection needle 6 is shifted on the outflow opening 11, the claws 26 then snapping behind the collar 17. When forcing the liquid outwards through the injection needle, the claws 45 on the lips 49 will be slightly bent towards each other by the opening 41, so that the lugs 50 can move along the collar 61, and, thus, the piston can pull the needle fitting 60 with the needle 27 into the liquid container.

FIG. 9 shows the embodiment of the injection assembly according to FIG. 7 with the suction needle provided with a sheath 70. This sheath comprises, along its complete inner wall, longitudinal ribs 71 which can cooperate with the suction needle 4, which sheath, at 72, closely fits on the cap 9 of the suction needle 4, the latter being provided at its outer side with suitable ribs 74. This is also shown in the preceding Figs. Because of the presence of these ribs 74 and the close fitting 72, the suction needle can, in the presence of the sheath 70, easily be mounted on the outflow opening 11 and be removed therefrom.

FIG. 10 shows the same sheath, however mounted on an injection needle 6 according to FIG. 8, the lugs 71 then cooperating with a portion 75 of the cap 30 of the injection needle. Intentionally the injection needle is, not provided with ribs at 76, since this needle should only be mounted and not be removed. With other words, as shown in FIG. 10, only a force in the direction of the arrow A is to be exerted, and not in the other sense.

FIG. 11 shows a special embodiment of an injection assembly according to the invention, the principle of operation thereof corresponding with that of the assembly according to FIGS. 8 and 9, i.e. the simplified embodiment of FIGS. 6 and 7, but, now, a special sheath 80 is used. This sheath 80 comprises two sheath portions 81 and 82, the suction needle 4 already being mounted on the outflow opening 11, and the sheath portion 81 of the injection needle 6 being closed by means of a cap 83. In this case the liquid container, as shown in FIGS. 12 and 13, is made oval. FIG. 12 shows a section along the line X—X of FIG. 11, and FIG. 13 an end view of the sheath 80. As clearly follows therefrom, the shape of the piston 3 is adapted accordingly.

The advantage of this special embodiment is that the suction needle and the injection needle can be supplied as one part, so that both cannot get lost, and, moreover, can be easily exchanged. When the suction needle is mounted, the sheath 80 can be removed, and the liquid container can be filled with the liquid. Subsequently the suction needle is inserted into the sheath portion 82, and is removed from the outflow opening 11. The cap 83 is, then, removed from the sheath portion 81, and can, if required, be placed in the opening 85, whereafter the injection needle 6, still present in the sheath portion 81, is snapped on the outflow opening. Subsequently the sheath can be thrown away, since, after use, the injection needle is retracted into the liquid container.

For this embodiment, and also for the preceding ones, holds that the cross-section of the liquid container is not restricted to a specific form, and is, preferably, substantially oval or approximately polygonal. In the embodiment of FIGS. 1–4 a non-circular shape of the liquid container is specifically preferred, since, for instance, an oval liquid container is more easily deformable during lifting the lugs 12 than a circular one.

FIG. 14 shows, finally, a perspective view of a piston 3 comprising a front surface 90, a piston rod 91 and four supports 92 supporting an annular collar 94. This embodiment is a special one since such a piston can be manufactured in a relatively simple manner. This piston comprises a central recess in the piston head with an inwardly directed collar. This piston can be manufactured by means of a simple two-part die with only one filling piece 95. The separation of the die-halves is schematically indicated on the piston 3 by means of a dotted line 97. After completion a rubber piston cap 98 can be arranged, as shown in section in FIG. 15.

I claim:

1. In an injection assembly that includes:

a liquid container with an outflow opening, a piston displaceable in said liquid container, wherein a suction needle with a needle fitting is adapted to be releasably fitted on the outflow opening of the liquid container, and an injection needle with a needle fitting which is adapted to be permanently fixed on the outflow opening of the liquid container, the piston comprising:

(a) first coupling means which are adapted to be coupled directly with the needle fitting of the injection needle, so as to allow the injection needle to be retracted into the liquid container after use;

(b) safety means preventing the first coupling means of the piston from forming a coupling during displacement of the piston in the presence of the suction needle; and an auxiliary coupling part including second coupling means which are coupled with the first coupling means of the piston in the presence of the injection needle, but which cannot couple with the first coupling means in the presence of the suction needle.

2. The injection assembly of claim 1, wherein the auxiliary coupling part is formed as a substantially funnel-shaped part which substantially fits in the extremity of the liquid container near the outflow opening, said auxiliary coupling part further including third coupling means which are permanently coupled with a portion of the needle fitting of the injection needle to be inserted into the outflow opening, the second coupling means of the auxiliary coupling part being in the form of one or more claws, the first coupling means on the piston then having the form of an annular collar with which the claws form a permanent coupling, in that the liquid container includes, near the second coupling means of the auxiliary coupling part, at least one lug for positioning the auxiliary coupling part, which lug is released by the piston, and wherein the suction needle fitting includes a portion to be inserted into the outflow opening and has such a length that the claws of the auxiliary coupling part in the presence of the suction needle cannot be coupled with the annular collar on the piston.

3. The injection assembly of claim 2, wherein said third coupling means are formed as at least one lip curved towards the longitudinal axis of the assembly, the portion of the suction needle fitting to be inserted into the outflow opening including an annular groove for accommodating said at least one lip, and the portion of the injection needle fitting to be inserted into the outflow opening includes a collar for a permanent coupling with the lips.

4. The injection assembly of claim 1, wherein the auxiliary coupling part is substantially tubular, the second coupling means being in the form of at least one lip with claws and includes a, third coupling means comprising an annular groove which on the one hand can releasably cooperate with the needle fitting of the suction needle and on the otherhand can be coupled with the needle fitting of the injection needle, the claws of the second coupling means being adapted to cooperate with a recess in the extremity of the piston, and wherein the outflow opening is provided at the inner side with a fourth coupling means with two positions which are adapted to cooperate with a fifth coupling means at the outer side of the auxiliary coupling part, all this in such a manner, that, on the one hand in the presence of the suction needle, the claws of the second coupling means cannot cooperate with the recess in the piston and the fifth coupling means can cooperate with the fourth coupling means in the first position, and, on the other hand in the presence of the injection needle, the claws of the second coupling means can cooperate with the recess in the piston, since, when putting on the injection needle, the coupling between the fourth and the fifth coupling means is brought into the second position.

5. The injection assembly of claim 4, wherein said fifth coupling means of the auxiliary coupling part are in the form of lugs on the lips of the claws of the second coupling means, and wherein said fourth coupling means are formed on the inner wall of the outflow opening in the form of two circumferential recesses, the recess at the downflow side seen in the outflow direction of the outflow opening being chamfered towards the other recess, all this in such a manner, that, on the one hand after inserting the auxiliary coupling part into the outflow opening and in the presence of the suction needle, the lugs on the lips of the claws can cooperate with the downflow recess, at which moment the claws of the second coupling means cannot be coupled with the piston, and, on the other hand when putting on the injection needle, the lugs on the auxiliary coupling part can be moved into the other recess, at which moment a coupling of the claws with the piston is possible, during which coupling the coupling between the lugs and the recess can be released by bending the lips towards each other.

6. The injection assembly of claim 5, wherein the auxiliary coupling part forms a part of the needle fitting of the injection needle.

7. The injection assembly of claim 6, wherein the fourth coupling means are made in the form of a circumferential recess or collar at the inner side of the outflow opening, with which the fifth coupling means can cooperate for coupling the auxiliary coupling part with the liquid container, which coupling can be released by coupling the piston with the auxiliary coupling part and by bending the lips towards each other.

8. The injection assembly of claim 6, wherein the outflow opening of the liquid container is made in the form of a tube section having a chamfered collar, and wherein the needle fittings of the suction as well as the injection needle include a cap having an inner diameter which is smaller than the outer diameter of the chamfered collar.

9. The injection assembly of claim 4 wherein the auxiliary coupling part forms a part of the needle fitting of the injection needle.

10. The injection assembly of claim 9, wherein the fourth coupling means are made in the form of a circumferential recess or collar at the inner side of the outflow opening, with which the fifth coupling means can cooperate for coupling the auxiliary coupling part with the liquid container, which coupling can be released by coupling the piston with the auxiliary coupling part and by bending the lips towards each other.

11. The injection assembly of claim 9, wherein the outflow opening of the liquid container is made in the form of a tube section having a chamfered collar, and wherein the needle fittings of the suction as well as the injection needle include a cap having an inner diameter which is smaller than the outer diameter of the chamfered collar.

12. The injection assembly of claim 11, wherein the cap of the injection needle includes at least one claw which can be permanently coupled with the chamfered collar on the outflow opening.

13. The injection assembly of claim 1, wherein the suction needle as well as the injection needle comprise a sheath which is removed before use.

14. The injection assembly of claim 13, wherein sheaths are united as two sheath portions of one sheath.

15. The injection assembly of claim 14, wherein the sheaths portions are united with one another to one sheath and wherein the needles are inserted therein side by side but in the opposite direction, at least one sheath portion comprising a closing cap which also fits on the other sheath portion.

16. An auxiliary coupling part, intended for being used in an injection assembly according to claim 1.

17. An injection needle, comprising a needle and a needle fitting, intended for an injection assembly according to claim 1.

18. A suction needle, comprising a needle and a needle fitting, intended for an injection assembly according to claim 1.

19. A sheath for an injection assembly according to claim 1, including two oppositely directed sheath portions, intended for accommodating a suction needle and an injection needle.

20. A piston with a recess provided with an inwardly directed collar in the extremity thereof for use in an injection assembly according to claim 1, comprising a piston rod with a front surface directed substantially transversely thereto, on which front surface an annular collar portion is supported by two or more supports, around which assembly a suitably shaped elastically deformable piston head is arranged.

* * * * *

UNITED STATES PATENT AND TRADEMARK OFFICE
CERTIFICATE OF CORRECTION

PATENT NO. : 5,466,226

DATED : November 14, 1995

INVENTOR(S) : van der Haak

It is certified that error appears in the above-identified patent and that said Letters Patent is hereby corrected as shown below:

| Column | Line | |
|---|---|---|
| 1 | 38 | After "can" insert --be--. |
| 1 | 65 | Change "An other" to --Another--. |
| 1 | 67 | Change "more easily" to --easier--. |
| 3 | 17 | Change "On" to --At--. |
| 4 | 6 | After "This" insert --is--. |
| 6 | 22 | Change "de" to --the--. |
| 6 | 35 | Delete "inwards". |
| 6 | 36 | After "needles" insert --inwards--. |
| 6 | 55 | Change "and will be" to --without being--. |

UNITED STATES PATENT AND TRADEMARK OFFICE
CERTIFICATE OF CORRECTION

PATENT NO.  : 5,466,226
DATED       : November 14, 1995
INVENTOR(S) : van der Haak It is certified that error appears in the above-identified patent and that said Letters Patent is hereby corrected as shown below:

| Column | Line | |
|--------|------|---|
| 8  | 12 | After "Intentionally" insert --,--; after "is" delete ",". |
| 8  | 14 | Change "With" to --In--. |
| 8  | 16 | Change "sense" to --direction--. |
| 8  | 44 | Delete "holds that". |
| 9  | 48 | After "claws" insert --,--. |
| 9  | 49 | After "a" delete ",". |
| 9  | 51 | Change "otherhand" to --other hand--. |
| 10 | 63 | Change "sheaths" to --sheath--; change "to one" to --to form one--. |

Signed and Sealed this

Twenty-first Day of May, 1996

Attest:

BRUCE LEHMAN

Attesting Officer　　　Commissioner of Patents and Trademarks